United States Patent [19]
Shearing

[11] Patent Number: 5,154,696
[45] Date of Patent: Oct. 13, 1992

[54] PHACOEMULSIFICATION, IRRIGATION AND ASPIRATION METHOD AND APPARATUS

[76] Inventor: Steven P. Shearing, P.O. Box 27212, Las Vegas, Nev. 89126

[21] Appl. No.: 681,811

[22] Filed: Apr. 8, 1991

[51] Int. Cl.$^5$ .............................. A61B 17/36
[52] U.S. Cl. ................. 604/22; 128/24 AA; 128/898; 606/107; 606/169; 606/171
[58] Field of Search ............ 604/22; 128/24 AA, 898; 606/107, 128, 169, 171

[56] References Cited

U.S. PATENT DOCUMENTS 3,589,363  6/1971  Banko et al.
3,736,938  6/1973  Evvard et al. ............ 606/169
3,996,935  12/1976  Banko .

FOREIGN PATENT DOCUMENTS 229003  7/1987  European Pat. Off. ............ 606/169
1034746  8/1983  U.S.S.R. ............ 604/22

OTHER PUBLICATIONS

Manual of Cataract Surgery by Sinskey, et al., pp. 53-69, 1987.
Cataract by Shearing et al., pp. 6-11, Jan. 1985.
Iolab-Newsletter "Cross-Hairs" Nov. 1988.

Primary Examiner—Randall L. Green
Assistant Examiner—Mary Beth O. Jones
Attorney, Agent, or Firm—Bradford E. Kile; Kevin M. O'Brien; Ruffin B. Cordell

[57] ABSTRACT

In a method and apparatus for phacoemulsification cataract surgery, a primary handpiece operable for phacoemulsification, irrigation and aspiration is inserted through a first incision in the limbus of an eye at a 12 o'clock position. An auxiliary handpiece for aspiration is inserted during the phacoemulsification, irrigation and aspiration operative procedure through a smaller second incision at approximately a three o'clock position. Both handpieces are fluidly connected to a power source aspiration from either the primary or auxiliary handpieces by rotation of the valve.

14 Claims, 4 Drawing Sheets

PHACOEMULSIFICATION, IRRIGATION AND ASPIRATION METHOD AND APPARATUS

BACKGROUND OF THE INVENTION

This invention relates to a method and apparatus for surgically removing a cataractous lens from a human eye. More specifically, this invention is directed to a safe and efficient method and apparatus of small incision, phacoemulsification, irrigation and aspiration of a cataract lens.

Through trauma, age, etc., a human natural crystalline lens may become opaque or cloudy and thus ceases to clearly transmit and focus light. This condition is referred to as a cataract or cataractous lens and is a leading cause of blindness in humans throughout the world.

In the last forty years or so techniques have been developed to surgically remove the cataract lens and replace it with an artificial or intraocular lens.

A cataract lens extraction process may be performed by a number of medically recognized techniques. A well-known and increasingly popular technique among ophthalmic surgeons is known as phacoemulsification, irrigation and aspiration.

Phacoemulsification involves placing two concentric tubes through a corneal incision of approximately three millimeters or so in length made in the region of the limbus where a colored portion of the eye meets a white portion of the eye. The innermost tube is ultrasonically vibrated and this vibrating tip member operably disintegrates the hard nuclear material of the cataract lens after the capsule or skin of the lens has been cut open.

In this type of surgery the vibrating inner tube also functions as an aspirator so that emulsified cataract lens material may be aspirated out of the eye. The outer tube functions as an irrigator allowing for inflow of saline fluid into the eye and preventing the cornea from collapsing as the lens material is being grounded up and aspirated. These concentric tubes at the tip of a handpiece of the system are operably attached to an external source of power, fluid and vacuum which provides for controlled ultrasonic vibration, irrigation and suction.

Once the nucleus of the lens has been ground up and aspirated the handpiece is changed. A new handpiece is used which does not have a vibrating inner tube but the inner tube is still designed to provide for aspiration. This new inner tube usually has a smaller opening at its tip which is rounded off, and usually is either 0.2 or 0.3 millimeters in diameter. This irrigation-aspiration (IA) handpiece is believed to be safer for removal of relatively soft cortical material or cortex which surrounds the hard nucleus of a lens.

It has long been recognized that the two tubes that constitute the handpiece need not be concentric; i.e., that the in-flow tube can be placed through a separate incision from the aspirating and/or vibrating tube. In 1970 the Sparta Corporation manufactured and sold a system with a separate inflow tube and a separate vibrating tube without any source of aspiration. The two tubes were placed through separate incisions and fluid was allowed to flow out around the vibrating tube without any actual aspiration. This system never achieved great popularity or support and is not believed to be currently available.

In the January 1985 issue of "Cataract International Journal of Cataract Surgery", applicant reported initial results of a system of separating an in-flow tube from a vibrating/suction tube and placing the tubes through two separate incisions. This system had the advantage of allowing the cataract to be removed through two small incisions of approximately 1.5 millimeter each. However, since almost all cataract wounds are opened to an incision size of 4 to 6 millimeters to allow for insertion of an intraocular lens this technique also did not gain popularity.

Initially in phacoemulsification the capsule or skin of the cataractous lens is opened at the start of the procedure by making multiple cuts in the skin in what is called often referred to as a "can opener" technique. This technique results in multiple small jagged edges in the anterior surface of the lens capsule. In the late 1980s a new technique for making the opening in the anterior capsule was introduced which has become popular. This technique is called capsulorhexis and involves making a relatively small and circular continuous tear in the anterior capsule which does not leave a jagged edge. Capsulorhexis is believed to exhibit many advantages for an ophthalmic surgeon. However, it has one serious disadvantage. Because the opening in the anterior capsule is relatively small it is difficult to manipulate the concentric tubes of the handpiece so as to remove the cortical material close to where the handpiece has been inserted. In this, if the outermost diameter of an iris is viewed as the face of a clock, then incision of the tip of a phacoemulsification handpiece into the eye is usually made at what is said to be a twelve o'clock position. With a capsulorhexis continuous tear anterior capsulotomy it is difficult to remove the 12:00 o'clock cortical material. Efforts have been made to overcome this problem by bending the tip of the handpiece or using other specialized instruments and techniques; however, none of these have proved to be entirely satisfactory.

The difficulties suggested in the proceeding are not intended to be exhaustive, but rather are among many which may tend to reduce the effectiveness and satisfaction with prior phacoemulsification, irrigation and aspiration method and apparatus appearing in the past. Other noteworthy problems may also exist. Those presented above, however, should be sufficient to demonstrate that phacoemulsification methods and apparatus appearing in the past will admit to worthwhile improvement.

OBJECTS OF THE INVENTION

It is therefore a general object of the invention to provide a novel phacoemulsification and aspiration method and apparatus which will obviate or minimize difficulties of the type previously described.

It is a specific object of the invention to provide a method and apparatus for phacoemulsification, irrigation and aspiration which rapidly and efficiently removes cortex tissue at an operative twelve o'clock position.

It is another object of the invention to provide a method and apparatus for phacoemulsification, irrigation and aspiration which advantageously utilizes relatively small incisions in the eye.

It is a further object of the invention to provide effective phacoemulsification, irrigation and aspiration method and apparatus with minimum trauma to eye tissues.

It is still a further object of the invention to enable an ophthalmic surgeon to practice the subject invention without discarding his/her current phacoemulsification equipment.

BRIEF SUMMARY OF A PREFERRED EMBODIMENT OF THE INVENTION

In a preferred embodiment of the invention, which is intended to accomplish at least some of the above objects, and in particular eliminating the problem of removal of the twelve o'clock cortex tissue following capsulorhexis and phacoemulsification cataract surgery, an auxiliary tube, cannula or needle and aspiration handpiece is inserted through a separate incision distant from the initial or primary incision for a phacoemulsification handpiece. This auxiliary handpiece is then connected to the irrigation and aspiration handpiece and a power and fluid supply source through a three-way valve. The three-way valve is connected at a location such that it can be readily controlled by an assistant. The three-way valve enables aspiration to be selectively applied through either the primary handpiece or the auxiliary handpiece.

Initially aspiration occurs through the innermost tube of the irrigation and aspiration handpiece in a conventional technique. However, the three-way valve allows for instantaneous reversal of the accessory handpiece and irrigation and aspiration handpiece so that the accessory handpiece can become the aspirator, while the IRRIGATION AND ASPIRATION handpiece remains the irrigator. Conversion of aspiration from the primary to accessory handpiece, while irrigation continues from the primary handpiece, allows an ophthalmic surgeon to approach the twelve o'clock cortex from an alternate direction or angle, thereby facilitating removal of the cortical material from the twelve o'clock area. Moreover in many instances it may be desirable to alternate back and forth between the primary and auxiliary handpiece to facile and efficiently remove emulsified cataract tissue.

THE DRAWINGS

Figure 4:
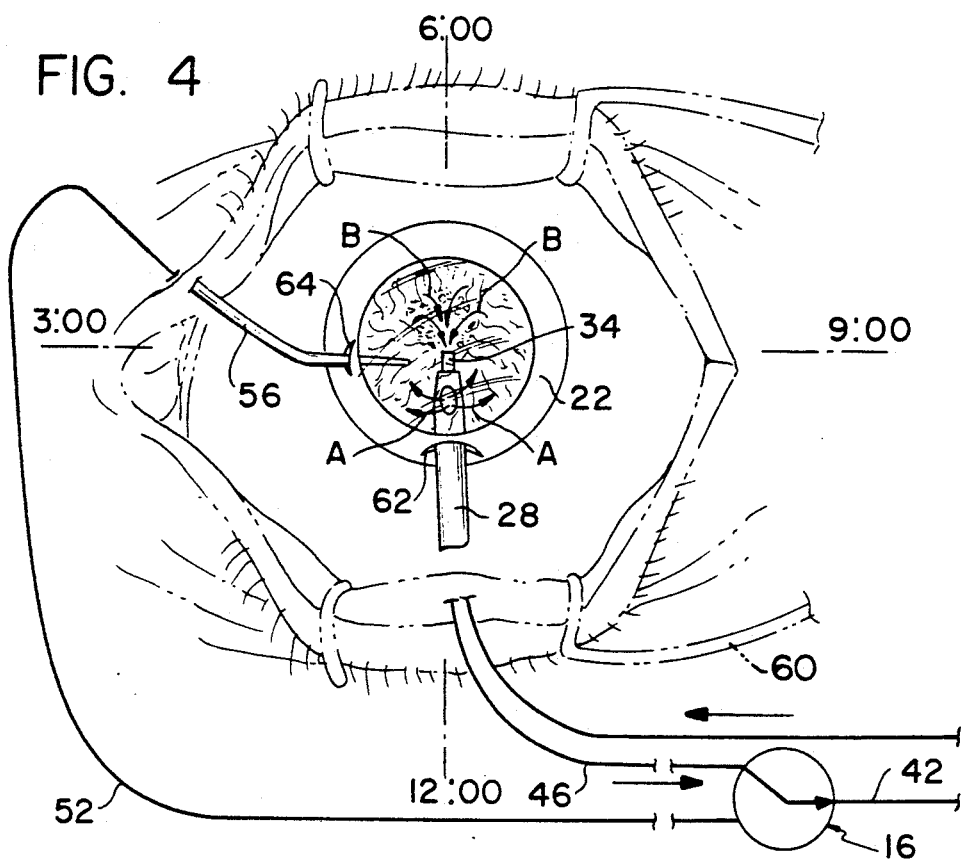
FIG. 4 is a schematic view of the eye of a patient depicting initial phacoemulsification and removal of the nucleus of a cataract lens where a primary handpiece is inserted through the cornea in a limbus position at approximately a twelve o'clock position.
Figure 5:
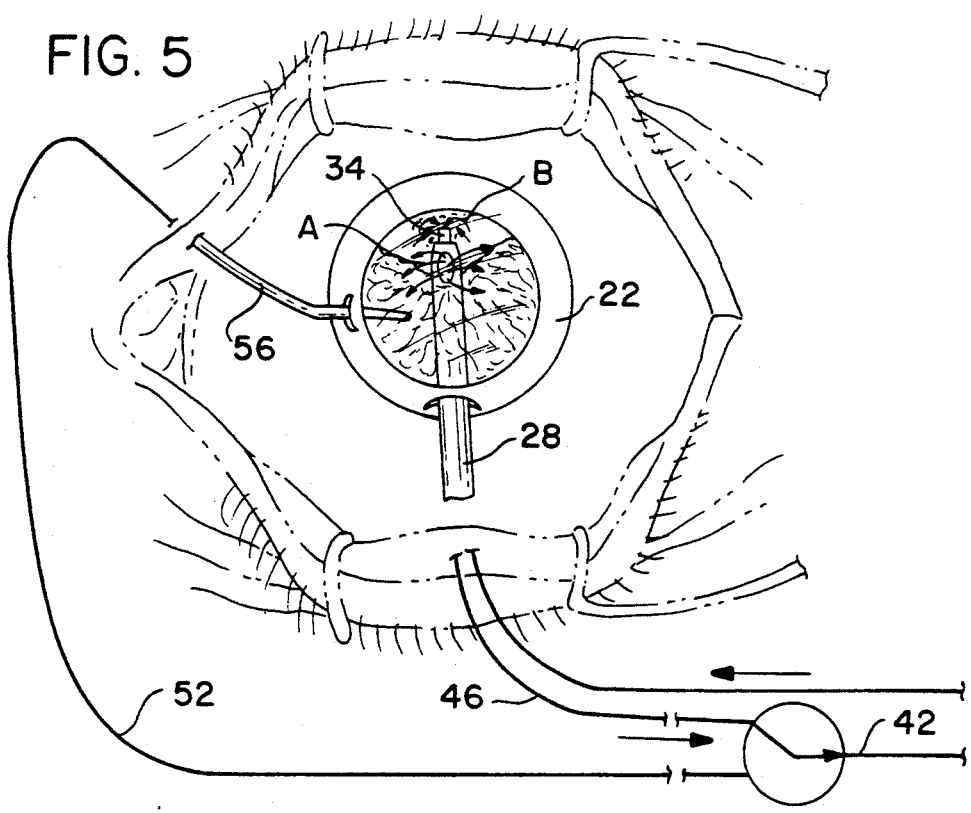
FIG. 5 is a schematic view similar to FIG. 6 depicting initial removal of the cataract lens at a six o'clock position of the lens.
Figure 6:
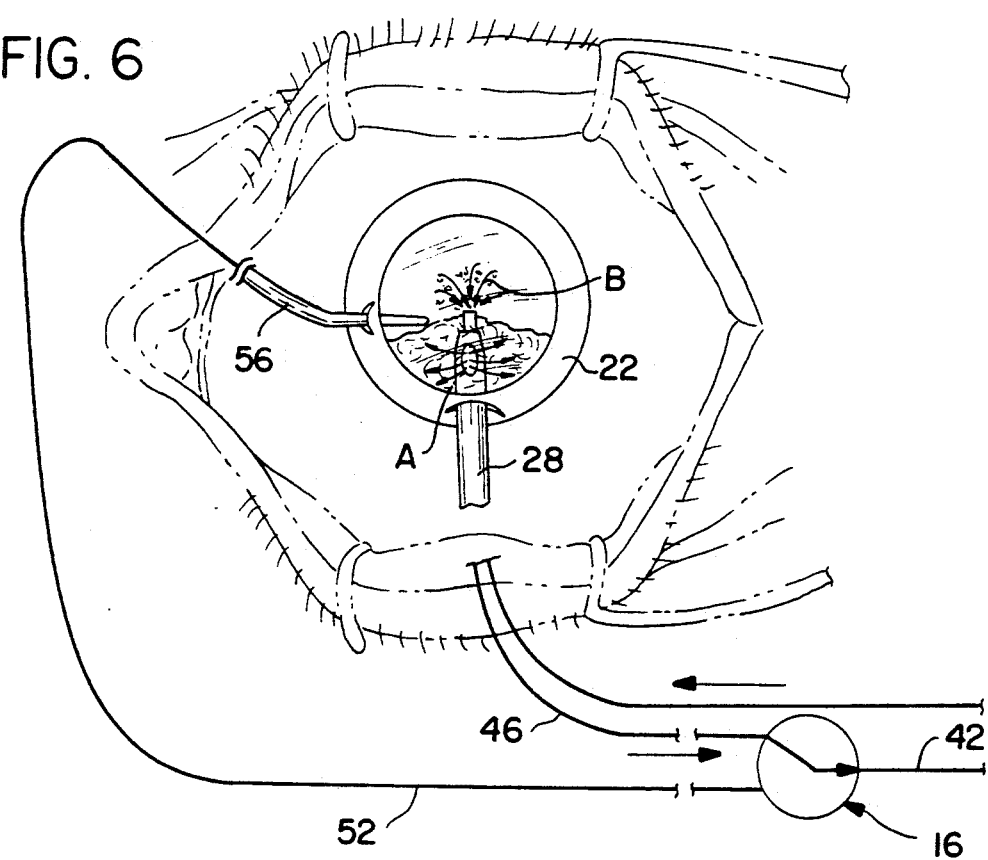
Figure 7:
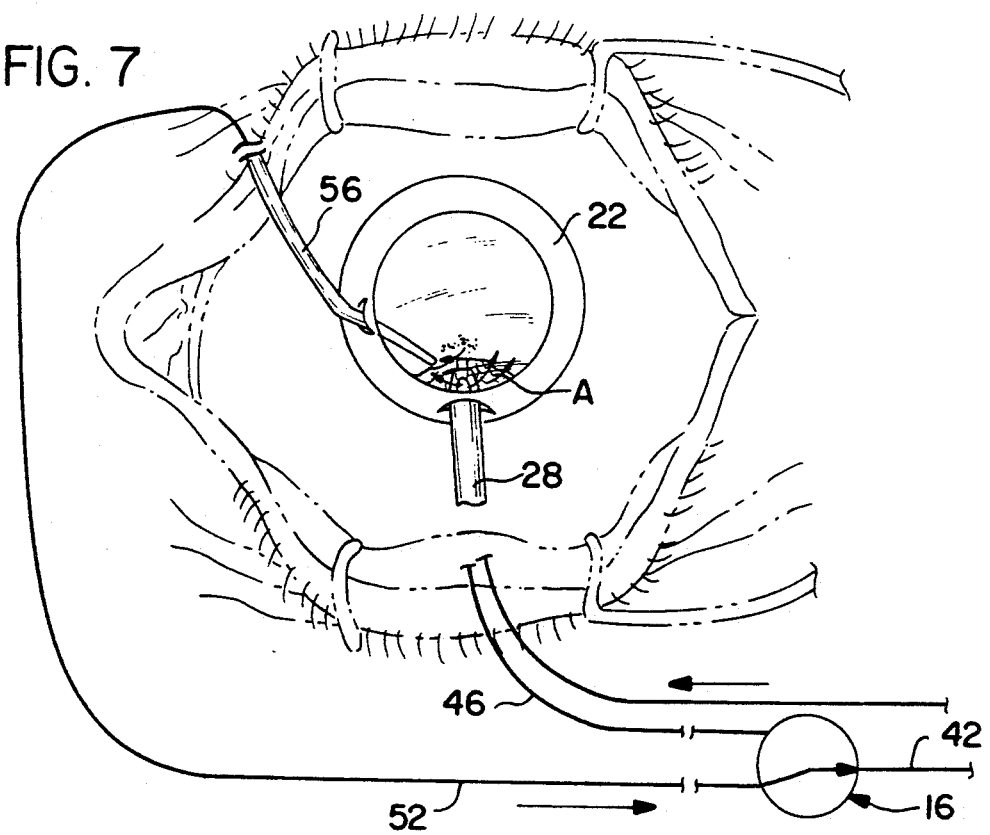

FIG. 6 is a further schematic view in sequence to FIGS. 4 and 5 and discloses removal of most of the cataract nucleus by utilization of the primary handpiece; and FIG. 7 is a final schematic view, in sequence with FIGS. 4, 5 and 6, and discloses removal of the twelve o'clock and surrounding cortex tissue with a secondary aspiration handpiece which has been activated by rotation of a three-way valve.

DETAILED DESCRIPTION

Figure 1:
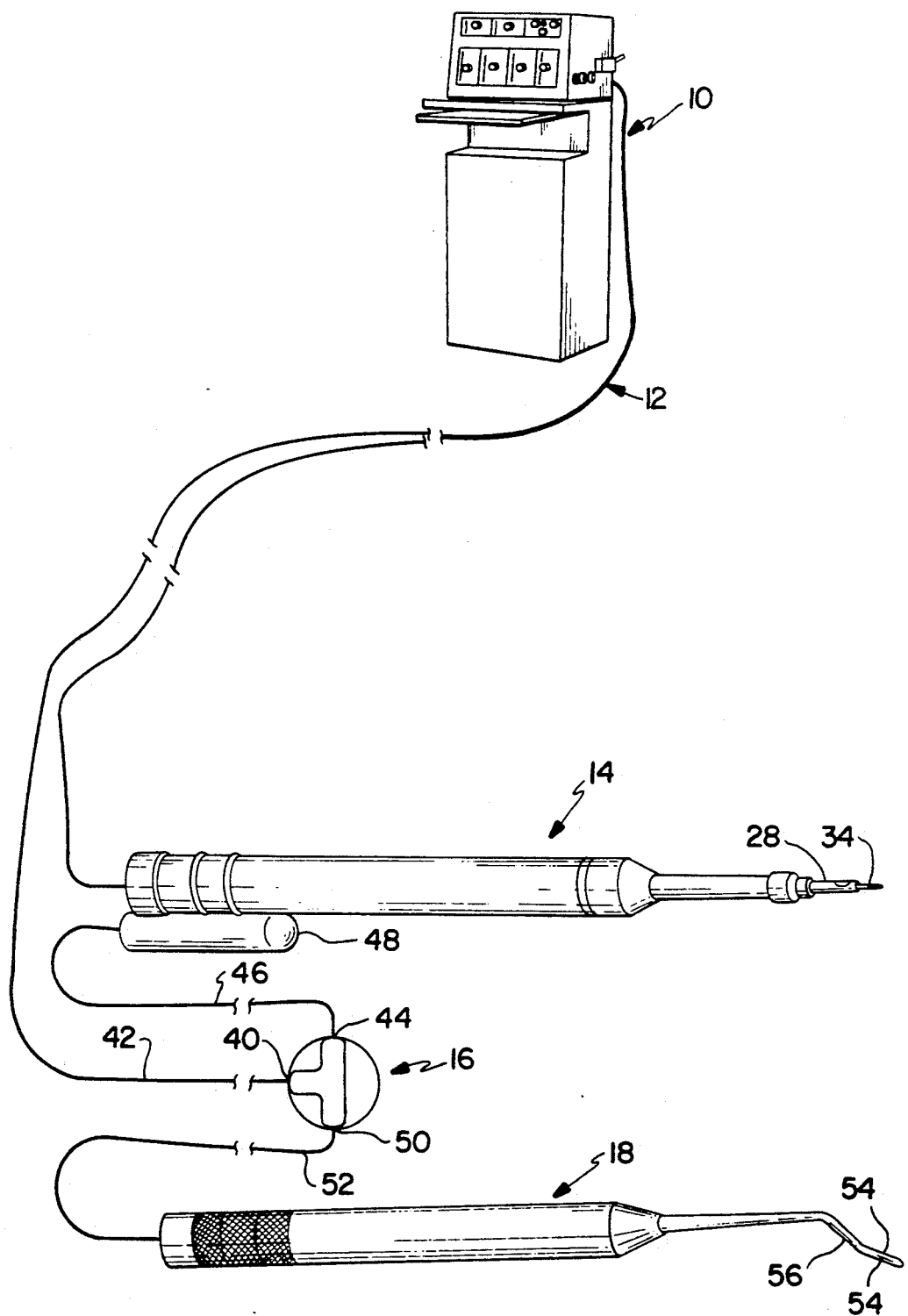
FIG. 1 is a schematic, axonometric view of a phacoemulsification, irrigation and aspiration system utilizing a primary and secondary handpiece in accordance with a preferred embodiment of the subject invention.

Turning now to the drawings wherein like numerals indicate like parts, and by reference to FIG. 1, there will be seen a power source 10, of a conventional design, suitable to provide phacoemulsification, fluid irrigation and aspiration of emulsified cataract lens tissue from a human eye. In this connection, a bundled conduit 12 extends from the power unit 10 and includes an electrical line for providing electromagnetic vibration, to be discussed below, a saline or similar sterile fluid irrigation line and a return vacuum line for aspiration of emulsified cataract tissue suspended in a fluid irrigating media.

As further shown in FIG. 1, electrical and irrigating fluid from the power source 10 is connected via the bundle of lines 12 to a first or primary handpiece 14 suitable for phacoemulsification and irrigation. In addition, a vacuum or aspiration conduit extends from the power source 10 and is connected to a three-way valve 16 which in turn is fluidically connected to the primary hand piece 14 and the auxiliary or secondary handpiece 18 for aspiration of an emulsified and suspended cataract tissue.

Context of the Invention

A detailed description of the subject invention, it may be worthwhile to outline an operating context of the invention.

Figure 2:
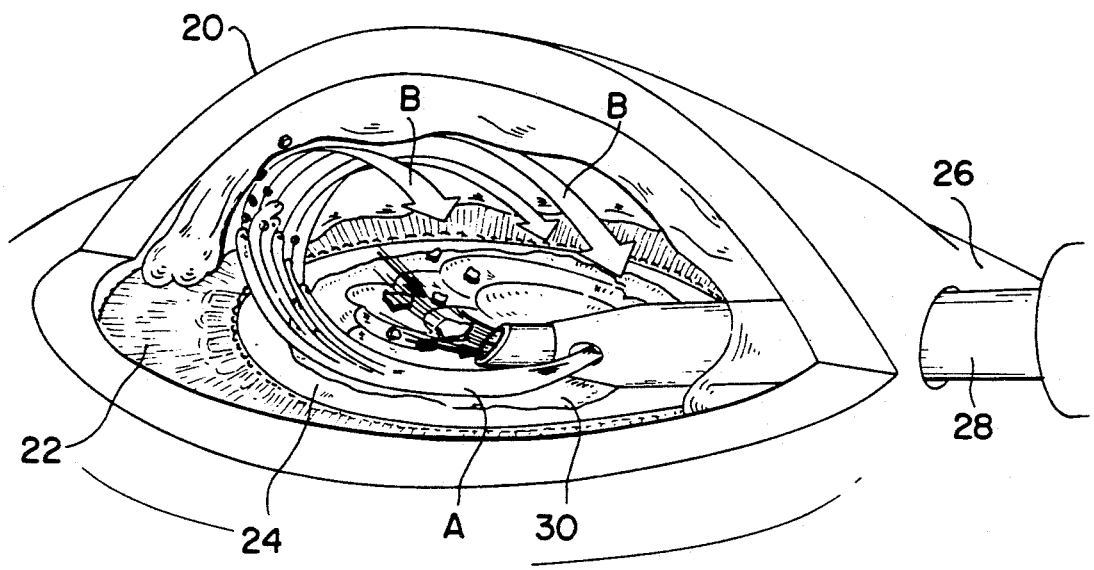
FIG. 2 is a partially broken away axonometric view of the primary removal process of necular abstract material of a lens by conventional phacoemulsification, irrigation and aspiration.

Referring now to FIG. 2, there will be seen an illustration of the cornea 20 of a human eye which is a generally arcuate segment in front of an iris diaphragm 22. The region between the iris and the cornea 20 is known as the anterior chamber of the human eye. Directly behind the iris 22 is a lens capsule 24, and in a healthy eye, a natural crystalline convex lens is in-housed within the capsule 24 for focusing light, in cooperation with the cornea, upon the retina of a human eye. Through trauma, age or other causes, the natural crystalline lens may become cloudy, in the nature of milk glass, and fail to transmit and focus light in a proper manner. When this condition exists, a patient is said to have a cataract lens and the patient becomes functionally blind in the eye. Cataracts are a leading cause of blindness throughout the world, however in the last 40 years or so, as noted above, ophthalmic surgeons have been successful in removing the cataract lens and replacing it with an artificial or intraocular lens.

A currently preferred technique for removing a cataract lens is known as phacoemulsification, irrigation and aspiration. In this, an opening 26, typically three to three and one-half millimeters in length is surgically fashioned through a limbus portion of the eye. This opening serves to admit the tip of a phacoemulsification, irrigation and aspiration tool. The tip of the tool 28 is operably extended through the cornea and into juxtaposition with cataract lens tissue 30. In this regard, the forward or anterior surface of the lens capsule 24 is first removed utilizing in many instances a currently preferred technique of capsulorhexis where a relatively small and continuously circular tear is made in the anterior capsule without creating jagged edges around the opening as illustrated in FIG. 2.

Figure 3:
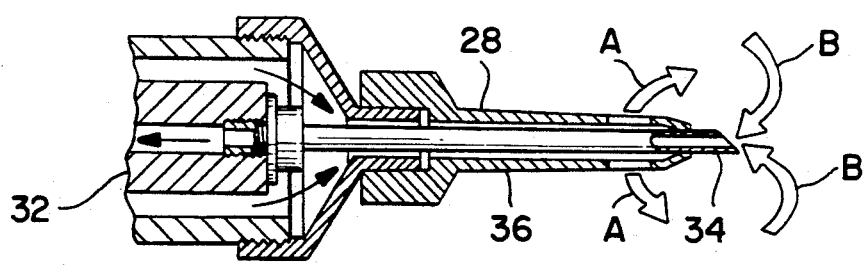
FIG. 3 is a cross-sectional view of the operative end of a phacoemulsification, irrigation and aspiration handpiece disclosed in FIG. 1.

Referring now to FIG. 3, a cross sectional view is illustrated of the tip of a conventional phacoemulsification, irrigation and aspiration handpiece. Internally an electromagnetic core 32 is ultrasonically excited from the power source 10. The core rapidly vibrates at between 10,000 and 100,000 cycles per second and preferably at about 25,000 cycles per second. This rapid ultrasonic vibration serves to vibrate an inner tube 34 which is brought into physical contact with a cataract nucleus. The rapid vibrating tip 34 physically emulsifies or breaks up the cataract, note again FIG. 2. Concomitantly an irrigation fluid, from the power source 10, is supplied to a surrounding annulus within the handpiece and irrigating fluid is laterally emitted from the flexible tip member 36 as indicated generally by directional arrows "A" in FIGS. 2 and 3. The irrigating fluid serves to commingle with and operably suspend bits of emulsified cataract tissue within the anterior chamber. As further illustrated in FIGS. 2 and 3, a vacuum is drawn on the bore of the tip portion 34. This vacuum serves to pull the irrigating fluid and suspended cataract material co-axially through the tip 34 as shown by direction arrows "B" and back to a collection reservoir at the power supply 10.

Three-way Valve and Auxiliary Hand Unit

Returning now to FIG. 1, one feature of the instant combination invention is the provision of a three-way valve 16 and an auxiliary handpiece 18 to facilitate aspiration of an emulsified cataract lens. More particularly, the threeway valve 16 includes three operative internal passages. A first passage is connected to the source of vacuum in the power supply 10 via a fluid conduit 42. A second passage 44 in the three-way valve 16 is connected via fluid conduit 46 to a vacuum manifold member 48 which in term is connected to the primary hand piece 14. The manifold member 48 includes a plentum operable to fluidically connect into a central conduit through the primary handpiece 14 for operably receiving return irrigating fluid and suspended cataract tissue indicated by directional arrow in FIG. 3. A third passage 50 is fashioned into the three-way valve and operably connects to a fluid conduit 52 which in turn is connected to the auxiliary or secondary handpiece 18. The handpiece 18 is fashioned with a lateral apertures 54 in opposing sides of a tip, note FIG. 1. These apertures serve to receive irrigating fluid and emulsified and suspended cataract lens material upon selective rotation of the three-way valve 16.

Method of Phacoemulsification, Irrigation and Aspiration

Turning now to FIGS. 4-7, there will be seen in a series of sequential views depicted a method of phacoemulsification, irrigation and aspiration of a cataract lens in accordance with a preferred embodiment of the invention.

Turning specifically to FIG. 4, it will be seen that a patient's eye has been draped and is held in an open position by standard expanding clamp 60. An initial incision 62, of approximately 3 millimeters in length, is fashioned through the cornea in the limbus region and an anterior segment of the lens capsule is removed by a capsulorhexis technique. The tip 28 of a phacoemulsification, irrigation and aspiration hand tool is inserted through the relatively small incision 62. In this, the outside diameter of the tip 2 is slightly less than three millimeters in diameter to fit through the incision 62. The vibratory tip 34 is manipulated into physical engagement with the relatively hard nucleus material of the cataract and serves to emulsify the nucleus. Concomitantly irrigating fluid is injected into the capsular region and anterior chamber as indicated by arrows A in FIG. 4. The irrigating fluid serves to maintain valve and suspend particulate portions of the cataract nucleus. In addition, and simultaneous with the emulsification and irrigation, a vacuum is drawn through the bore of the vibrating tip 34 as indicated with arrows B. The suspended cataract material is withdrawn or aspirated out of the capsular bag through the tip 34 and fluid lines 42 and 46 back to a receiving reservoir at the power station 10. In this connection, the three-way valve 16 is positioned as indicated schematically in FIG. 4 to provide fluid connection between vacuum lines 42 and 46.

In addition, to the three millimeter primary incision 62 a relatively smaller one millimeter incision 64 is fashioned through a limbus portion of the cornea at an angle with respect to the initial incision 62 and the tip 28 of the phacoemulsification handpiece. In this connection, if the eye of a patient is imagined as a clock face with the initial incision 62 being made at a twelve o'clock position, as noted in FIG. 4, in a preferred embodiment the second incision 64 is positioned at approximately a three o'clock position. The tip 56 of the secondary handpiece 18 is then positioned snugly through the second incision.

The tip 56 of the secondary auxiliary handpiece has an outside diameter of slightly less than one millimeter which enables an ophthalmic surgeon to facile insert the auxiliary tip 56 into position adjacent to the cataract lens being emulsified. During an initial emulsification, irrigation and aspiration procedure the three-way valve 16 remains in the position indicated. Aspiration is not normally provided through the auxiliary handpiece 56.

Focusing now on FIG. 5, it will be seen that the tip of the primary handpiece 14 has been inserted into a posture wherein the ultrasonically vibrating tip 34 is utilized to erode away or emulsify the cataract in a six o'clock region of the lens. Aspiration is provided through the central bore of the tip 34 is serving to substantially removing the emulsified cataract lens material permitting light to pass in the general six o'clock region.

FIG. 6 is a sequential view of the phacoemulsification, irrigation and aspiration process depicted in FIGS. 4 and 5 wherein an ophthalmic surgeon has manipulated the primary handpiece such that the cataract lens has been substantially emulsified in over half of the lens and aspirated through the tip 34 of the primary handpiece. As shown in FIG. 6, the three-way valve remains closed to the auxiliary handpiece while open to the primary handpiece. Thus aspiration continues as previously indicated with respect to FIGS. 4 and 5.

Turning now to FIG. 7, the ophthalmic surgeon has substantially removed the cataract lens material from the lens capsule, however in a position in the region of twelve o'clock such as from approximately from 10:30 to 1:30 o'clock there remains lens tissue or cortex tissue which has been found to be somewhat difficult to remove via the primary handpiece during small incision surgery.

At this time, an assistant is directed to rotate the three-way valve 16 and stop aspiration through the primary handpiece via line 46 and begin aspiration through the auxiliary handpiece tip 56 via line 52. This auxiliary handpiece 56 maybe faciley manipulated to aspirate cortex tissue away from the region of twelve o'clock. Moreover, cortex tissue in any peripheral region of the capsule may be drawn into a central region of the capsule and in a preferred embodiment an ophthalmic surgeon may choose to selectively rotate the three-way valve 16 back to its initial position thus bringing the aspiration power source via line 42 again into fluid communication with line 46 and utilize the primary tool again to aspirate emulsified cataract material from the lens capsule. In the event further cortex tissue remains, a surgeon may again reverse the three-way valve and manipulate the auxiliary handpiece as desired to remove remaining bits of cataract tissue.

Once the emulsified cataract lens material is completely removed from the lens capsule both the primary and secondary handpieces are withdrawn. The secondary incision, being relatively small, is self healing and typically does not require a suture.

Although the invention has been discussed with respect to initial and/or intermittent aspiration through the primary handpiece, it is a further aspect of this invention that primary aspiration occur through the secondary or auxiliary handpiece.

SUMMARY OF MAJOR ADVANTAGES OF THE INVENTION

After reading and understanding the foregoing description of the subject invention, in conjunction with the accompanying drawings, it will be appreciated that several distinct advantages of the phacoemulsification, irrigation and aspiration method and apparatus of the subject invention are obtained. Specifically the provision of small incision during the surgical procedure provides for a minimum intrusion of the cortex tissue of the eye. Moreover, the small incision 64 in a lateral portion of the eye, for reception of an auxiliary hand tool, in most cases, requires no suture for closure. In a related aspect the small incision surgery permits the reduction of irrigating fluid for full aspiration of the cataract lens.

Still further, the subject invention provides a method and apparatus wherein aspiration of emulsified cataract lens material is facilitated particularly around the twelve o'clock position and the surgical procedure may be performed more rapidly then with conventional techniques while providing a minimum amount of trauma to the eye tissue.

The three-way valve enables an ophthalmic surgeon flexibility over the aspiration process to quickly and efficiently access, position and remove cortex tissue at a twelve o'clock and other peripheral regions as needed.

In describing the invention, reference has been made to a preferred embodiment and illustrative advantages of the invention. Those skilled in the art, however, am familiar with the disclosure of the subject invention may recognize additions, deletions, modifications, substitutions and/or other changes which fall within the purview of the subject invention and claims.

What is claimed is:

1. A method of phacoemulsification, irrigation and aspiration of a cataract lens from the eye of a human comprising the steps of:
    forming a first incision in the region of the limbus of a human eye at approximately a twelve o'clock position;
    forming a second incision in the eye offset from said first incision;
    opening an anterior segment of a lens capsule containing a cataract lens;
    inserting a tip portion of a primary handpiece operable for phacoemulsification, irrigation and aspiration of a cataract lens through the first incision and into juxtaposition with the cataract lens through the anterior segment opening;
    inserting a tip portion of an auxiliary handpiece for aspiration, at some point during the phacoemulsification, irrigation and aspiration operative procedure, through the second incision and into juxtaposition with the cataract lens wherein the tip portion of the auxiliary handpiece extends at an angle with respect to the primary handpiece;
    utilizing the primary handpiece, emulsifying a nucleus of the cataract lens through the opening in the anterior segment of the lens capsule and concomitantly irrigating and aspirating the emulsified nucleus of the cataract lens out of the lens capsule substantially throughout the lens capsule including in the regions of three o'clock, six o'clock and nine o'clock positions of the lens capsule;
    following phacoemulsification, converting an aspiration vacuum from the primary hand piece to the auxiliary handpiece while maintaining irrigation with the primary handpiece;
    aspirating any remaining emulsified cortex tissue generally from the twelve o'clock position of the lens capsule through the auxiliary handpiece; and
    removing the tip portions of the primary handpiece and auxiliary handpiece from the first and second incisions in the eye following full aspiration of the cataract lens from the lens capsule.

2. A method of phacoemulsification, irrigation and aspiration of a cataract as defined in claim 1 wherein said step of forming a second incision comprises:
    forming said second incision in the region of the limbus of the human eye at approximately a position offset ninety degrees from the first incision.

3. A method of phacoemulsification, irrigation and aspiration of a cataract as defined in claim 1 wherein said step of forming a second incision comprises:
    forming said second incision in the limbus of the human eye at approximately a three o'clock position.

4. A method of phacoemulsification, irrigation and aspiration of a cataract as defined in claim 1 wherein said steps of forming first and second incisions comprises:
    forming said first incision of approximately three millimeters in length; and
    forming said second incision at approximately a three o'clock position of approximately one millimeter in length.

5. A method of phacoemulsification, irrigation and aspiration of a cataract as defined in claim 1 wherein said step of converting aspiration from the primary handpiece to the auxiliary handpiece comprises:
    rotating a three way valve connected to a vacuum source from fluid communication with the primary handpiece to fluid communication with the secondary handpiece.

6. A method of phacoemulsification, irrigation and aspiration of a cataract as defined in claim 1, 4 or 5 wherein said step of opening an anterior segment comprises:
    utilizing a capsulorhexis technique of making a relatively small and continuous circular tear in the anterior capsule without creating substantial jagged edges around the opening in the anterior capsule.

7. A method of phacoemulsification, irrigation and aspiration of a cataract lens from the eye of a human comprising the steps of forming a first incision in the region of the limbus of a human eye at approximately a twelve o'clock position;

forming a second incision in the eye offset from said first incision;

opening an anterior segment of a lens capsule containing a cataract lens utilizing a capsulorhexis technique;

inserting a tip portion of a primary handpiece operable for phacoemulsification, irrigation and aspiration of a cataract lens through the first incision and into juxtaposition with the cataract lens through the anterior segment opening;

inserting a tip portion of an auxiliary handpiece for aspiration, at some point during the phacoemulsification, irrigation and aspiration operative procedure, through the second incision and into juxtaposition with the cataract lens wherein the tip portion of the auxiliary handpiece extends at an angle with respect to the primary handpiece;

utilizing the primary handpiece, emulsifying a nucleus of the cataract lens through the opening in the anterior segment of the lens capsule and concomitantly irrigating the emulsified nucleus of the cataract lens;

aspirating the emulsified cataract from the lens capsule by selectively converting an aspiration vacuum back and forth as surgically indicated between the auxiliary handpiece and the primary handpiece while maintaining irrigation from the primary handpiece.

removing the tip portions of the primary handpiece and auxiliary handpiece from the first and second incisions in the eye following full aspiration of the cataract lens from the lens capsule.

8. A method of phacoemulsification, irrigation and aspiration of a cataract as defined in claim 7 wherein said steps of forming first and second incisions comprises:

forming said first incision of approximately three millimeters in length; and forming said second incision at approximately a three o'clock position of approximately one millimeter in length.

9. A method of phacoemulsification, irrigation and aspiration of a cataract as defined in claim 7 wherein said step of selectively converting aspiration back-and-forth between the primary handpiece to the auxiliary handpiece comprises:

rotating a three way valve connected to a vacuum source from fluid communication selectively between the primary handpiece and the secondary handpiece.

10. An apparatus for phacoemulsification, irrigation and aspiration for removing a cataract from a human eye, said apparatus comprising:

power means for providing phacoemulsification, irrigation and aspiration of a cataract lens;

a primary handpiece connected to said power means having a tip for insertion through a first incision in the region of the limbus of the human eye at approximately a twelve o'clock position and for emulsifying, irrigating and aspirating a cataract lens from a lens capsule;

an auxiliary handpiece connected to said power means for insertion through a second incision offset from the first incision for selectively aspirating cataract tissue from the lens capsule; and means connected to each of said primary handpiece and said auxiliary handpiece for selectively connecting the aspiration portion of said power means to said primary handpiece or said auxiliary handpiece such that an ophthalmic surgeon may utilize said primary handpiece for phacoemulsification and irrigation of a cataract lens and for aspiration of the emulsified cataract lens material said primary handpiece and said auxiliary handpiece.

11. An apparatus for phacoemulsification, irrigation and aspiration as defined in claim 10 wherein:

the tip of said primary handpiece is less than three millimeters in diameter; and the tip of said auxiliary handpiece is less than one and one-half millimeters in diameter.

12. An apparatus for phacoemulsification, irrigation and aspiration as defined in claim 10 wherein said means for selectively connecting comprises:

a three-way fluid valve having a first branch operably connected to said power means for emulsifying, irrigating and aspirating, a second branch operably connected to said primary handpiece and a third branch operably connected to said auxiliary handpiece such that an operator may selectively connect said power means to said primary handpiece or said auxiliary handpiece.

13. An apparatus for adapting a cataract lens phacoemulsification, irrigation and aspiration system having a primary handpiece operable for phacoemulsification, irrigation and aspiration of emulsified cortex material through the primary handpiece and a fluid removal conduit connected to a vacuum source for aspiration of said emulsified cataract lens material comprising:

a three-way fluid valve having first, second and third fluid ports and being operable for connection at said first port to said fluid removal conduit;

a first conduit connected at one end to said second port of said three-way fluid valve and operable to be connected at the other end to said primary handpiece such that emulsified cataract lens material may be aspirated away from a lens capsule of a human eye through said primary handpiece;

an auxiliary handpiece having a tubular tip with at least one hole for insertion through an incision in a human eye and receiving emulsified cataract lens material from a capsular bag member of the eye; and a second conduit connected at one end to said third port of said three-way valve and connected at the other end to said auxiliary hand piece such that an ophthalmic surgeon may switch the aspiration function during phacoemulsification, irrigation and aspiration surgery selectively between a primary handpiece and an auxiliary handpiece for facile removing emulsified cataract lens material.

14. An apparatus for adapting a cataract lens phacoemulsification, irrigation and aspiration system as defined in claim 13 wherein:

said tubular tip of said auxiliary handpiece has an exterior diameter of approximately one millimeter in diameter.

* * * * *